United States Patent [19]
Marquardt et al.

[11] Patent Number: 5,866,378
[45] Date of Patent: Feb. 2, 1999

[54] PROCESS FOR THE SYNTHESIS OF NUCLEOTIDE-6-DEOXY-D-XYLO-4-HEXULOSES

[75] Inventors: Ruediger Marquardt, Frankfurt; Brigitte Hoersch, Kriftel; Andreas Seiffert-Stoeriko, Frankfurt; Andreas Stein, Juelich, all of Germany; Astrid Zervosen, Welkenraedt, Belgium; Lothar Elling, Aachen, Germany; Maria Regina Kula, Niederzier-Hambach, Germany; Stefan Verseck, Wuppertal, Germany; Juergen Distler, Wuppertal, Germany; Wolfgang Piepersberg, Wuppertal, Germany

[73] Assignee: Hoechst Aktiengesellschaft, Frankfurt, Germany

[21] Appl. No.: 731,189

[22] Filed: Oct. 7, 1996

[30] Foreign Application Priority Data

Oct. 6, 1995 [DE] Germany .................. 195 37 217.4

[51] Int. Cl.⁶ ............................ C12P 19/02; C12P 19/30; C12P 19/04; C12N 11/18
[52] U.S. Cl. .............................. 435/105; 435/89; 435/90; 435/101; 435/174; 435/175; 435/180; 536/22.1; 536/124
[58] Field of Search ............................... 435/89, 90, 101, 435/105, 174, 715, 180; 536/22.1, 124

[56] References Cited

U.S. PATENT DOCUMENTS 4,039,382  8/1977  Thang et al. ............................ 194/28 X

FOREIGN PATENT DOCUMENTS 42 21 595  9/1993  Germany .

OTHER PUBLICATIONS

A. Zervosen et al. "Combined Enzymatic Synthesis of Nucleotide (Deoxy) Sugars from Sucrose and nucleoside Monophosphates," *Tetrahedron*, vol. 52, No. 7, pp. 2395–2404, 1996.

L. Elling, "Effect of Metal Ions on Sucrose Synthase from Rice Grains—A Study on Enzyme Inhibition and Enzyme Topography", Glycobiology, vol. 5, No. 2, (1995), pp. 201–206.

L. Elling et al., "Investigation of Sucrose Synthase from Rice for the Synthesis of Various Nucleotide Sugars and Saccharides", Glycobiology, vol. 3, No. 4, (1993), pp. 349–355.

L. Elling et al., "Purification of Sucrose Synthase from Rice and its Protein–Chemical Characterization", Journal of Biotechnology, vol. 29, (1993), pp. 277–286.

C. H. Wong et al., "Regeneration of Sugar Nucleotide for Enzymatic Oligosaccharide Synthesis: Use of Gal–1–Phosphate Uridyltransferase in the Regeneration of UDP–Galactose, UDP–2–Deoxygalactose, and UDP–Galactosamine", J. Org. Chem., vol. 57, (1992), pp. 4343–4344.

K. Marumo et al., "Enzymatic Synthesis and Isolation of Thymidine Diphosphate–6–deoxy–D–xylo–4–hexulose and Thymidine Diphosphate–L–Rhamnose", Eur. J. Biochem., vol. 204, (1992), pp. 539–545.

A. Melo et al., "The Nucleotide Specificity and Feedback Control of Thymidine Diphosphate D–Glucose Pyrophosphorylase", J. Bio. Chem., vol. 240, (1965), pp. 398–405.

C. H. Wong et al., "Enzyme–Catalyzed Synthesis of N–Acetyllactosamine with in Situ Regeneration of Uridine 5–Diphosphate Glucose and Uridine 5–Diphosphate Galactose", J. Org. Chem., vol. 47, (1982), pp. 5416–5418.

J. E. Heidlas et al., "Nucleoside Phosphate Sugars: Synthesis on Practical Scales for Use as Reagents in the Enzymatic Preparation of Oligosaccharides and Glycoconjugates", Acc. Chem. Res, vol. 25, (1992), pp. 307–314.

C. H. Wong et al., "Probing the Acceptor Specificity of β–1,4–Galactosyltransferase for the Development of Enzymatic Synthesis of Novel Oligosaccharides", J. Am. Chem. Soc., vol. 113, (1991), pp. 8137–8145.

Y. Ichikawa et al., "Chemical–Enzymatic Synthesis and Conformational Analysis of Sialyl Lewis X and Derivatives", J. Am. Chem. Soc., vol. 114, (1992), pp. 9283–9298.

S. A. DeFrees et al., "Ligand Recognition by E–Selectin: Synthesis, Inhibitory Acitivity, and Conformational Analysis of Bivalent Sialyl Lewis X Analogs", J. Am. Chem. Soc., vol. 117, pp. 66–79.

H. Zarkowsky et al., "The Mechanism of 6–Deoxyhexose Synthesis", J. Bio. Chem., vol. 244, No. 17 (Sep. 1969), pp. 4750–4756.

S. Chang et al., "An Epimerase–Reductase in L–Fucose Synthesis", J. Bio. Chem., vol. 261, No. 1 (Feb. 1988), pp. 1693–1697.

A. Zervosen et al., "Kontinuierliche Enzymatische Synthese von 2'–Desoxythymidin–5'–(α–D–Glucopyroanosyl)–diphosphat", Agnew. Chem., vol. 106, (1994), pp. 592–593.

*Primary Examiner*—David M. Naff
*Attorney, Agent, or Firm*—Foley & Lardner

[57] ABSTRACT

The present invention relates to processes for the enzymatic synthesis of nucleotide-6-deoxy-D-xylo-4-hexuloses starting from a nucleoside monophosphate (NMP). These processes comprise simultaneous incubation of the following substances in a buffer solution:

(a) substrates comprising a nucleoside monophosphate, phosphoenolpyruvate, adenosine triphosphate, and sucrose; and (b) enzymes comprising pyruvate kinase, nucleoside-monophosphate kinase, sucrose synthase and deoxythymidine-D-glucose 4,6dehydratase.

11 Claims, 3 Drawing Sheets

| UDP-Gal | = uridine diphosphate-galactose |
| UDP | = uridine diphosphate |
| UDP-Glc | = uridine diphosphate-glucose |
| GlcNAc | = N-acetylglucosamine |
| LacNAc | = N-acetyllactosamine |
| Glcα1→2 Fru | = sucrose |
| Fru | = fructose |

| 1) | = sucrose synthase |
| 2) | = UDP-Gal epimerase |
| 3) | = ß-1→4-Galtransferase |

Products: R = CH₃ : dTDP-4-Keto-5-deoxyglucose
R = H : dUDP-4-Keto-6-deoxyglucose

FIG. 3

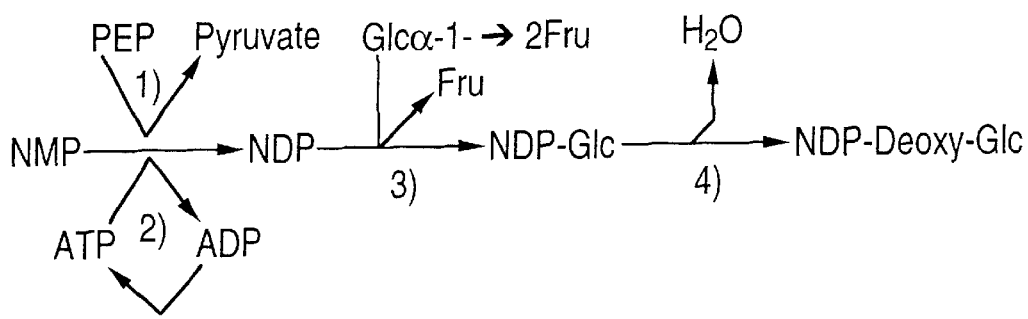

| NMP | = | Nucleoside monophosphate (for example dTMP, dUMP, UMP) |
| --- | --- | --- |
| NDP | = | Nucleoside diphosphate (for example dTDP, dUDP, UMP) |
| NDP-Glc | = | NDP-Glucose |
| NDP-deoxy-Glc | = | NDP-6-Deoxy-D-xylo-4-hexulose |
| PEP | = | Phosphoenolpyruvate |
| Glcα-1→2-Fru | = | Sucrose |
| Fru | = | Fructose |
| ATP | = | Adenosine triphosphate |
| ADP | = | Adenosine diphosphate |
| 1) | = | Pyruvate kinase |
| 2) | = | NMP kinase (NMPK) |
| 3) | = | Sucrose synthase |
| 4) | = | dTDP-D-Glc 4,6-dehydratase |

PROCESS FOR THE SYNTHESIS OF NUCLEOTIDE-6-DEOXY-D-XYLO-4-HEXULOSES

BACKGROUND OF THE INVENTION

Enzymatic syntheses of oligosaccharides (such as N-acetyllactosamine (LacNAc) and its derivatives), using glycosyltransferases (for example β-1→4-galactosyltransferase (GalT) [EC 2.4.1.38]) and nucleoside phosphate glycosides (nucleotide-sugars) as glycosyl donors have been known for a long time (Wong, C.-H., et al., J. Am. Chem. Soc. 118, 8137–8145, 1991). Wong et al. developed LacNAc syntheses in which the nucleotide-sugar, the uridine diphosphate-glucose (UDP-Glc), is regenerated in situ. See Wong, C.-H., et al., J. Org. Chem. 47, 5416–5418 (1982) and Wong, C. -H., et al. J. Org. Chem. 57, 4343–4344, (1992). As a consequence of this, it is no longer necessary in these reactions to employ the relatively costly nucleotide-sugars in stoichiometric amounts.

The LacNAc cycle developed by Elling and Kula (DE P 42 21 595 C1; Elling, L., Grothus, M., Kula, M.-R., Glycobiol. 3, 349–355, (1993)) represents an improvement compared with cycles disclosed to date, because only three enzymes have to be employed for the synthesis of LacNAc, instead of the six enzymes used in prior art methods. See FIG. 1. Such synthesized disaccharides can be used as precursors for further reactions with different transferases, for example sialyltransferases or fucosyltransferases.

The demand for nucleotide-sugars as substrates has grown in past years due to the discovery and utilization of glycosyltransferases for the preparation of oligosaccharides. It was this development which resulted in a demand to prepare these costly nucleotide sugar substrates at minimum cost in order to more easily obtain defined glycosyl structures.

One target product of these enzymatic syntheses is, for example, the tetrasaccharide sialyl-LewisX or its derivatives (Ichikawa, Y., et al., J. Am. Chem. Soc. 114, 9283–9298 (1992)), whose importance in cell-cell recognition is the subject of intensive research. See DeFrees, S., et al., J. Am. Chem. Soc. 117, 66–79, (1995).

Sucrose synthase [EC 2.4.1.13] is a glycosyltransferase which is widespread, especially in plants, and whose function as catalyst for the formation of nucleotide-sugars within plant metabolism has been reviewed in Avigad, G., Encyclopedia of Plant Physiology New Series Vol. 13A, Carbohydrates I, Intracellular Carbohydrates, Springer Verlag, Berlin, 217–347, (1982). This enzyme is suitable for synthesizing nucleotide-sugars, for example UDP-, dTDP-, ADP-, CDP- and GDP-Glc (Elling, L., Grothus, M., Kula, M.-R., Glycobiol. 3, 349–355, 1993). Purification of sucrose synthase from rice (Elling, L., Kula, M.-R., J. Biotechnol. 29, 277–286, 1993), and its use for in situ regeneration of UDP-Glc has been described by Elling et al. (DE P 42 21 595 C1; Elling, L., et al., Glycobiol. 3, 349–355, 1993). The rice enzyme is a homotetrameric protein with a molecular weight of 362 kDa. The enzyme has already been employed for the preparative synthesis dTDP-Glc starting from dTDP in an enzyme membrane reactor (EMR) (Zervosen, A., et al., Angew. Chem. 106, 592–593, (1994).

The increased availability of sucrose synthase in recent years has been made possible by purification studies such as those described by Elling (DE P 42 21 595 C1; Elling, L., et al., J. Biotechnol. 29, 277–286 (1993); Elling, L., et al., Glycobiol. 3, 349–355 (1993)). The enzyme itself has been known for several years, but insufficient amounts have been available to date to permit its protein chemical properties to be investigated.

Thus, only recently have the pH optimum, and the ions necessary for the reaction (ionic strength, presence of ions indispensable for the reaction) and the regulation of this enzyme (end product inhibition) become known (L. Elling, Glycobiology 5, 201–206, 1995). In addition while the enzyme is not commercially available, the isolation procedure for sucrose synthase is described in Elling, et al. Biotechnol 29:277–286 (1993), Elling, et al. Glycobiol. 3:349–355 (1993), and DE patent 42 21 595 C1, all of which are hereby incorporated by reference.

Preparative syntheses of nucleotide-sugars starting from a nucleoside monophosphate (NMP) have already been described (Heidlas J. E., Williams K. W., Whitesides G. M., Acc. Chem. Res., 25., 307–314, 1992). Heidlas discloses the conversion of NMP to nucleoside triphosphate (NTP) using myokinase and pyruvate kinase, which then reacted with the particular sugar 1-phosphate to give the nucleotide-sugar with catalysis by a specific pyrophosphorylase. In contrast to the nucleoside-specific pyrophosphorylases used in such processes, use of the enzyme sucrose synthase makes it possible to prepare variously activated glucose donors. Hence, it has now been found that sucrose synthase is able to accept both nucleotide diphospates (NDP) and deoxy nucleotide diphosphates (dNDP) as substrates. Thus, for example, dUDP-glucose can be prepared preparatively starting from sucrose as glycosyl donor and dUDP. Coupling kinase and sucrose synthase enzymatic reactions results in less costly production of nucleotide-sugars. Nucleoside monophosphates (NMP) can be used in such a coupled synthesis and can be obtained at distinctly lower cost than nucleoside diphosphates (NDP).

Some primary nucleotide-sugars are enzymatically converted in cells into other, so-called secondary nucleotide-sugars. Thus, for example, GDP-fucose is produced from GDP-mannose in three consecutive steps. Some recent findings in this area have been worked out by Chang et al. taking the example of porcine salivary glands (J. Biol. Chem., 263, 1693–1697, 1988). In this study, the authors describe the conversion of GDP-mannose first into GDP-4-keto-6-deoxymannose using a specific dehydratase, subsequently an epimerase and reductase activity to GDP-fucose. Direct preparation of fucose starting from mannose cannot take place in metabolism without the presence of the nucleotide group. These enzymes therefore rely on an activation, i.e. the nucleotide moiety. Based on the current state of research, it is likely that the formation of other secondary nucleotide-sugars takes place in a similar fashion. The nucleotide-sugars dUDP-and dTDP-6-deoxy-D-xylo-4-hexulose are formed via catalysis using dTDP-Glc-4,6-dehydratase [EC 4.2.1.46] from dUDP-and dTDP-Glc (Zarkowsky, H., Glaser, L., J. Biol. Chem. 222, 4750–4756, 1969). dTDP-6-Deoxy-D-xylo-4-hexulose is an intermediate product in the biosynthetic pathway of the dTDP-L-rhamnose. Enzymatic synthesis and isolation of such a have been described (Marumo, K., Lindqvist, L., Verma, N., Weintraub, A., Reeves, P. R., Lindberg, A. A., Eur. J. Biochem. 204, 539–545, 1992). dUDP-Glc cannot be bought but has been synthesized in analytical amounts using the dTDP-Glc pyrophosphorylase from Pseudomonas aeruginosa (Melo, A., Glaser, L., J. Biol. Chem. 240, 398–405, 1965). It is possible by utilizing the synthetic potential of sucrose synthase to prepare dUDP-and dTDP-6-deoxy-D-xylo-4-hexulose starting from dUMP and dTDP respectively (FIG. 2) (Stein, A., Dissertation, Heinrich Heine University, Dusseldorf, 1995). However, in the process taught by Stein, et al. the separate enzymatic reactions required to produce such hexuloses are carried out in separate reaction vessels. In other words, (1)

the coversion of NMP to NDP, (2) the transfer of the glucose moiety to dTDP or dUDP and (3) the dehydration of glucose all take place in separate vessels and one reaction must be complete before the next step is initiated.

Thus, the prior art does not disclose a method for the synthesis of nucleotide sugars whereby all the reagents and enzymes necessary to produce a nucleotide-sugar from a NMP, sugar and phosphate source may be incubated together. In particular, the prior art does not teach a method whereby sucrose synthase can be incubated along with enzymes which require dUDP-glucose as a substrate, such as a dehydratase.

It would therefore be useful to have a method for making nucleotide-sugars in which all reagents and enzymes could be incubated together in the same reaction vessel. In particular, it would be advantageous to have a method where sucrose synthase and a dUDP-glucose dehydratase could be used together to produce nucleotide-6-deoxy-D-xylo-4-hexulose.

SUMMARY OF THE INVENTION

It is therefore an object of the present invention to provide a method for the preparation of nucleotide sugars that utilizes the enzyme sucrose synthase and deoxynucleotide substrates, whereby all the substrates and enzymes required to produce deoxynucleotide-sugars can be incubated together in one reaction vessel.

Thus, in one embodiment, the invention provides a process for the enzymatic synthesis of nucleotide-6-deoxy-D-xylo-4-hexuloses starting from a nucleoside monophosphate (NMP), which process comprises simultaneous incubation of the following substances in a buffer solution:

(a) substrates comprising a nucleoside monophosphate, phosphoenolpyruvate, adenosine triphosphate, and sucrose; and (b) enzymes comprising pyruvate kinase, nucleoside-monophosphate kinase, sucrose synthase and deoxythymidine-D-glucose 4,6-dehydratase.

In further embodiments, the invention provides such a process wherein said nucleoside monophosphate is deoxythymidine monophosphosphate (dTMP), deoxyuridine monophosphate (dUMP), or uridine monophosphate (UMP).

In other embodiments, the process of the invention may be carried out as a batch process, using an enzyme membrane reactor wherein said enzymes are immobilized in the membrane reactor, which is placed in buffer solution containing the necessary substrates.

In still another embodiment, the process of the invention is carried out by immobilizing the pyruvate kinase, nucleoside-monophosphate kinase, sucrose synthase and deoxythymidine-D-glucose 4,6-dehydratase on a solid carrier material and continuously percolating the buffer solution comprising the substrates over the carrier material.

In yet other embodiments, when the process of the invention is carried out using an enzyme membrane reactor or enzymes immobilized on a carrier, the buffer solution containing the substrates is recycled more than once over the membrane reactor or carrier.

Finally, the invention provides a process for the preparation of a nucleotide-6-deoxy-D-xylo-4-hexulose, wherein dUMP, PEP, ATP and sucrose are used as substrates and wherein the enzymes pyruvate kinase, nucleoside-monophosphate kinase, sucrose synthase and deoxythymidine-D-glucose 4,6-dehydratase are used and wherein all the enzymes and substrates are incubated together using a batch process.

BRIEF DESCRIPTION OF THE DRAWINGS

FIG. 3 shows the enzymatic synthesis of nucleotide-deoxysugars starting with nucleoside monophosphate.

DETAILED DESCRIPTION OF THE INVENTION

Figure 1:
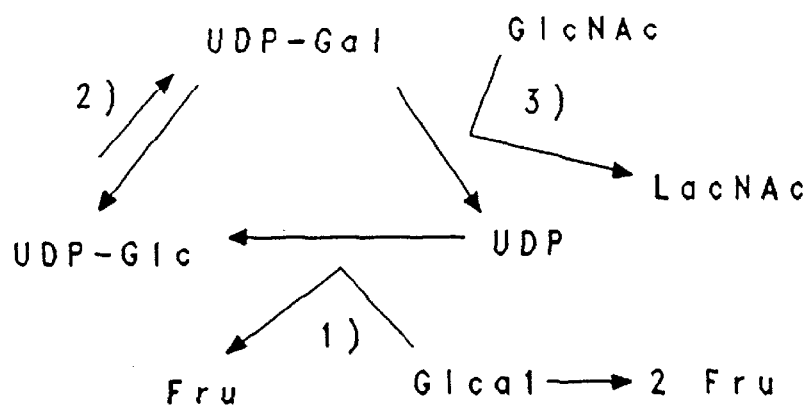
FIG. 1 shows the method for producing N-acetyllactosamine (LacNAc), described by Elling, et al. DE P42 21 595 C1 and Glycobiol. 3:349 (1993).
Figure 2:
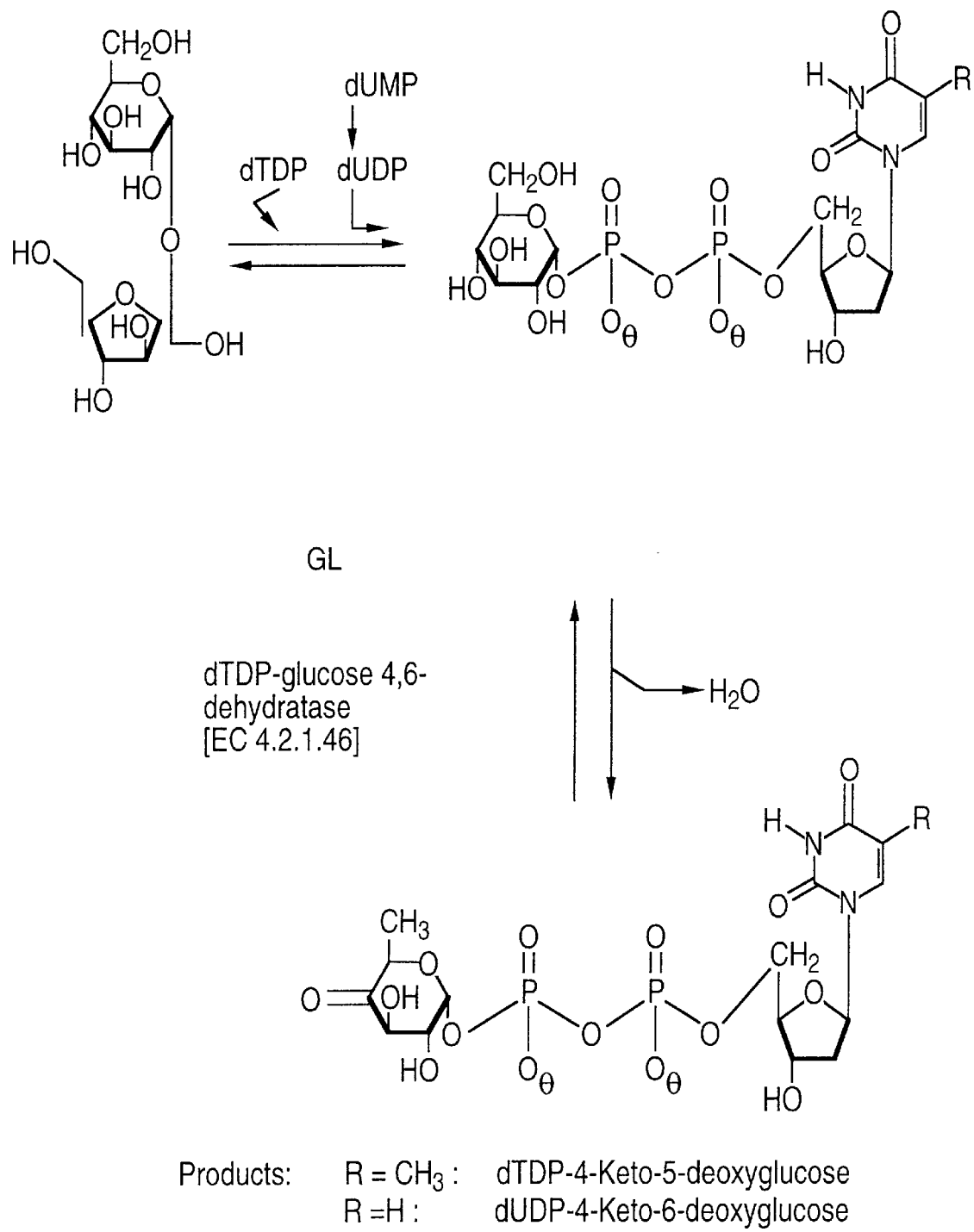
FIG. 2 shows the preparation of dTDP-6-deoxy-D-xylo-4hexulose, described by Stein, et al. Dissertation, Heinrich Heine University, Dusseldorf, 1995.

It has been found that during the preparation of nucleotide-sugars, sucrose synthase can be incubated with other enzymes at the same time leading to simple and novel possibilities for preparing nucleotide sugars, which are also known in the art as a type of "activated sugar." It has also been found that sucrose synthase can be incubated together with other enzymes which require dUDP-Glc as substrate. Thus, for example, sucrose synthetase can be incubated together with an NDP or a dNDP 4,6-dehydratase, which converts products further to secondary nucleotide-sugars. The NDP and dNDP 4,6-dehydratases are important enzymes for preparing activated deoxy sugars such as, for example, dTDP-L-rhamnose.

Thus, it is possible starting from NMP or dNMP to prepare costly NDP-sugars or dNDP-sugars using a process according to the invention. In particular, it is possible starting from NMP or dNMP, with addition of a pyruvate kinase, to prepare NDP or dNDP which is recognized by the sucrose synthase as substrate and is linked to glucose to give NDP-glucose or dNDP-glucose.

Accordingly, the present invention relates to a process for the enzymatic preparation of nucleoside diphosphate-6-deoxy-D-xylo-4hexuloses, wherein a nucleoside monophosphate, phosphoenolpyruvate (PEP), adenosine triphosphate (ATP) and sucrose (substrates), and pyruvate kinase, nucleoside-monophosphate kinase (NMPK), sucrose synthase and deoxythymidine-D-glucose 4,6-dehydratase (enzymes) are incubated simultaneously in a suitable buffer solution. The process of the invention is illustrated in FIG. 3.

Deoxythymidine monophosphate, deoxyuridine monophosphate or uridine monophosphate may be employed as the nucleoside monophosphate. The monophosphates of adenosine, of cytidine and of inosine are equally suitable for use in the process of the invention. The deoxy forms of these nucleosides are also suitable for use in the process of the invention.

The process of the invention may be carried out in an aqueous, buffered solution (for example Hepes, Tris, etc.). One suitable pH range is from 6 to 8, and one preferred pH range is from 7.2 to 7.5. One suitable temperature range is from 10° C. to 40° C., and one preferred temperature is 25° C. The skilled artisan will recognize that various reaction times may be used that are sufficient for synthesis of product. For example, any reaction time of up to 24 hours or up to about 24 hours may be used. One preferred time is anywhere from 0 to 24 hours, and another preferred time is 4 hours.

The process of the invention may also be carried out in an aqueous, buffered solution (for example Hepes, Tris, etc.), and a suitable pH range is from about 6 to about 8, and one preferred pH range is from about 7.2 to about 7.5. One suitable temperature range is from about 10° to about 40° C., and one preferred temperature is about 25° C. The reaction time may be anywhere from about 0 to about 24 hours, and one preferred time is about 4 hours.

The process according to the invention can be carried out using a batch process procedure or in a continuous fashion using an enzyme membrane reactor (EMR). In a batch process, all the enzymes and substrates are placed together in a single reaction vessel. In contrast, the EMR allows the reaction to proceed without the need for changing buffer solutions containing enzymes and substrates. Using an EMR, the enzymes are immobilized between the membranes in the reactor and placed in buffer solution containing the substrates. EMR are well known in the art. See, for example, Zervosen, supra. In one embodiment, the EMR is preferably equipped with an ultrafiltration membrane with an exclusion volume of less than 30,000 D so that the enzymes present in the reaction mixture are retained, while the low molecular weight products (activated sugars) and unreacted precursors pass through the membrane, and the product can be detected in the outflow. The reactor is preferably sterilized before use so that it is possible to avoid the addition of antibacterial substances (for example azide) which may adversely affect the enzyme activity.

The process according to the invention can also be carried out continuously by percolation of the solution which has been adjusted to a suitable pH and contains the precursors ((dNMP or NMP) or (dNDP or NDP)), sucrose, and other necessary substrates over a solid carrier material on which the appropriate enzymes have been immobilized. A suitable pH is from about pH 7 to about pH 7.5. One of skill in the art will appreciate that suitable carrier materials in this connection are commercially available carriers. (For example, Eupergit, CNBr-activated Sepharose, etc.). One of skill in the art will recognize that a suitable carrier will have functional groups which interact with the enzyme, e.g. by covalent bonds.

It is furthermore possible, both when the process is carried out in an EMR and when the solution is percolated over the immobilized enzymes, for the buffer solution containing the substrates to be recycled several times for repeated contact of substrates with the enzymes.

The dNDP- and NDP-activated sugars prepared according to the invention are purified by conventional processes known in the prior art. For example, the reaction mixture can be clarified by filtration or centrifugation, and then the enzymes can be removed by ultrafiltration (membrane with exclusion volume smaller than 30,000 Daltons), and remaining product can be washed out from between the membranes by diafiltration. Following such preparative steps, purification of the nucleotide sugars can be carried out using conventional methods such as gel chromatography (for example Sephadex oder Biogel), ion exchange or thin-layer chromatography, and HPLC or the like. See, for example, A. L. Demaire, MANUAL OF INDUSTRIAL MICROBIOLOGY AND BIOTECHNOLOGY.

The starting materials used in the process, such as, for example, dNMP or NMP, and dNDP or NDP, and sucrose, and the enzymes used, are commercially available and in the case of sucrose synthase can be prepared and isolated using processes described in the literature. See Elling, et al. Biotechnol. 29:277–286 (1993), Elling, et al. Glycobiol. 3:349–355 (1993), and DE patent 42 21 595 C1, all of which are hereby incorporated by reference.

The activated sugars prepared by the process according to the present invention can be used as "building blocks" for glycoconjugates. Such glycoconjugates are important, in particular, in the drug and agricultural sectors. In these, the nucleotide-activated sugar is used as substrate for a suitable glycosyltransferase which transfers the sugar to a suitable acceptor.

A suitable HPLC facility for analyzing the nucleotides and nucleotide-sugars consists of a model 300 C high-precision pump, an SP-6V UV spectrophotometer, a model CINA automatic sample collector, and a Chromapac C-R GA integrator (Gynkotek, Munich, FRG). Columns: 2×Aminex HPX-87H (300×7.8 mm) with a cation H+ exchanger cartridge (30×4.6 mm); eluent: 0.006M $H_2SO_4$; flow rate: 0.8 ml/min; detection: 205 nm.

The process according to the present invention is described in detail hereinafter by means of examples, which serve to illustrate, but not limit the invention.

EXAMPLE 1

Preparative synthesis of dUDP-glucose

Synthesis mixture:
247 mg of dUMP (Na salt, 4 mM, Sigma), 310 mg of PEP (Na salt, 6 mM, Sigma), 27.3 mg of $MgCl_2$, 13.6 mg of ATP (Na salt, 0.12 mM, Sigma), 25.7 g of sucrose (5 mM), total volume 150 ml. Buffer: Tris-HCl (100 mM, pH 7.2, 3 mM DTT, 1 mg/ml BSA) Enzymes: 40 U of sucrose synthase (2 U/ml), 400 U of pyruvate kinase (20 U/ml), 20 U of NMPK (1 U/ml). Reactor: 50 ml Amicon cell with YM30 membrane (used for concentration) Reaction volume: 20 ml run 1–6, 50 ml run 7 Incubation temperature: 37° C.

Product purification:
1) Cleavage of dUMP and dUDP with alkaline phosphatase [EC 3.1.3.1] from calf intestine (special quality for molecular biology from Boehringer Mannheim, Germany).

Mixture: 1 U of alkaline phosphatase/ml of product solution 17 hours at 30° C.

2) Removal of the proteins by YM10 ultrafiltration (using instructions provided by Amicon with YM10)

3) Ion exchange: anion exchange on Q-Sepharose FF (2.6×35.4 cm, volume : 4 ml/min, gradient: 0.5 l of $H_2O$ pH 7.0, 0.5 1 l of 300 mM LiCl pH 7.0).

4) Concentration of the solution in a rotary evaporator at 20–25 mbar and 35–40° C.

5) Desalting of the sample on G10 (2.6–93 cm, eluent: Millipore water pH =7.0)

6) Freeze-drying

7) Purification of UDP-Glc using chromatography.

For renewed anion exchange chromatography with Q-Sepharose FF, the pH of the product solution was adjusted to 7.0. It was possible to remove the pyruvate which was still present in the Sepharose by using a linear LiCl gradient (0.25 l of $H_2O$ pH 7.0, 0.25 l of 0.5 M LiCl pH 7.0) to elute the product (which was detected enzymatically). Purification steps 4–6 (above) followed.

EXAMPLE 2

Synthesis of dUDP-6-deoxy-D-xylo-4-hexulose starting from dUDP-Gic

Synthesis mixture:
20.1 mg of dUDPGlc (10 mM)
1920 µl of Hepes/NaOH (200 mM, pH 7.2, 1 mM DTT, 500 mM sucrose, 25 mM KCl, 1 mg/ml BSA)
80 µl of dTDP-D-Glc 4,6-dehydratase (1.48 U, crude extract)
Incubation at 30° C., incubation time: 4 h using a batch process procedure.

After 4 h no dUDP-Glc was detected using HPLC, indicating the reaction was complete.

Synthesis of dTDP-6-deoxy-D-xylo-4-hexulose took place under experimental conditions similar to those described above in this example. In this case, complete reaction was observed after only 1 h.

EXAMPLE 3

Synthesis of dUDP-6-deoxy-D-xylo-6-hexulose starting from dUMP

Synthesis mixture:
Volume =3 ml
4 mM dUMP (Na salt, Sigma), 4 mM PEP (CHA salt, Biomol), 0.8 mM $MgCl_2$, 0.12 mM ATP (Na salt, Sigma), 500 mM sucrose, 6 U of sucrose synthase (2 U/ml), 60 U of pyruvate kinase (20 U/ml), 3 U of NMPK (1 U/ml), 15 U of dTDP-D-Glc 4,6-dehydratase (5 U/ml), Buffer: Tris-HCl (100 mM, pH 7.5, 3 mM DTT, 1 mg/ml BSA, 50 mM KCl) Incubation temperature: 25° C.

The process was carried out using a batch process procedure. After an incubation time of 4 h, formation of 69.3% of dUDP-6-deoxy-D-xylo-6-hexulose was observed. Product yield was calculated using HPLC.

German Patent Application 19537217.4 (Oct. 6, 1995), the foreign priority document for the present application, is hereby incorporated by reference in its entirety, including the specification, claims, abstract and drawings.

We claim:

1. A process for the enzymatic preparation of nucleotide-6-deoxy-D-xylo-4-hexuloses, which process comprises simultaneous incubation of the following substances in a buffer solution:
   (a) substrates comprising a nucleoside monophosphate, phosphoenolpyruvate, adenosine triphosphate, and sucrose; and
   (b) enzymes comprising pyruvate kinase, nucleoside-monophosphate kinase, sucrose synthase and deoxythymidine-D-glucose 4,6-dehydratase.

2. The process of claim 1, wherein said nucleoside monophosphate is deoxythymidine monophosphate.

3. The process of claim 1, wherein said nucleoside monophosphate is deoxyuridine monophosphate.

4. The process of claim 1, wherein said nucleoside monophosphate is uridine monophosphate.

5. The process of claim 1, wherein said process is carried out as a batch process.

6. The process of claim 1, wherein said process is carried out using an enzyme membrane reactor, and wherein said enzymes are immobilized between the membranes of said reactor, which is in said buffer solution.

7. The process of claim 1, wherein said enzymes are immobilized on a solid carrier material and wherein said buffer solution comprising said substrates is percolated continuously over said carrier material.

8. The process of claim 6, wherein said buffer solution comprising said substrates is recycled more than once over said membrane reactor.

9. The process of claim 7, wherein said buffer solution comprising said substrates is recycled more than once over said solid carrier material.

10. The process of claim 1, wherein said nucleoside monophosphate is dUMP, and wherein said enzymes are immobilized between the membranes of an enzyme membrane reactor, and wherein said substrates are recycled more than once over said membrane reactor.

11. The process of claim 1, wherein said nucleoside monophosphate is dUMP, and wherein said enzymes and substrates are incubated using a batch process.

* * * * *